United States Patent [19]
Heise

[11] Patent Number: 4,937,881
[45] Date of Patent: Jul. 3, 1990

[54] GARMENT DEVICE FOR HANDLING AND STORING NOXIUOS MATERIALS

[75] Inventor: Annemarie Heise, Winnebago County, Wis.

[73] Assignee: Kimberly-Clark Corporation, Neenah, Wis.

[21] Appl. No.: 567,833

[22] Filed: Jan. 3, 1984

[51] Int. Cl.$^5$ .................. A41D 19/00; A47L 25/00; B65D 33/16

[52] U.S. Cl. ............................................ 2/16; 2/158; 2/161 R; 2/163; 2/167; 15/227; 36/7.1 R; 294/1.3; 383/93; 383/907

[58] Field of Search .................. 2/16, 167, 168, 159, 2/158, 240, 161 R, 53, 163; 223/111; 604/292; 206/438, 440; 294/1.3, 25; 383/72, 74, 75, 76, 77, 93, 127, 907; 15/227

[56] References Cited

U.S. PATENT DOCUMENTS

| | | | |
|---|---|---|---|
| 338,790 | 3/1886 | Slack | 2/159 |
| 720,640 | 2/1903 | Torrens | 2/168 |
| 1,241,941 | 10/1917 | Dowd | 2/168 |
| 1,731,340 | 10/1929 | Lambert | 2/158 |
| 2,497,749 | 2/1950 | Wagner . | |
| 2,700,161 | 1/1955 | Boyce | 2/240 |
| 2,741,410 | 4/1956 | LaViolette | 223/111 |
| 2,782,912 | 2/1957 | Humphrey | 2/158 |
| 2,972,748 | 2/1961 | Haynes . | |
| 3,074,399 | 1/1963 | Bitting | 2/158 |
| 3,276,670 | 10/1966 | Harvey | 383/77 |
| 3,372,799 | 3/1968 | Abildgaard . | |
| 3,543,999 | 12/1970 | Kugler | 383/76 |
| 3,588,916 | 6/1971 | Glatt | 2/53 |
| 3,676,887 | 7/1972 | Klein . | |
| 3,813,121 | 5/1974 | Marvin . | |
| 3,850,467 | 11/1974 | Johnson | 294/1 |
| 3,866,245 | 2/1975 | Sutherland | 2/167 |
| 3,885,249 | 5/1975 | Brabander | 2/158 |
| 4,132,442 | 1/1979 | Larsson | 294/1 |
| 4,215,886 | 8/1980 | Naderi et al. . | |
| 4,355,424 | 10/1982 | McCoy, Jr. . | |
| 4,445,230 | 4/1984 | Spadaro | 383/76 |

FOREIGN PATENT DOCUMENTS

| | | | |
|---|---|---|---|
| 1018117 | 10/1976 | Canada | 294/1.3 |
| 856133 | 6/1939 | France . | |
| 1017712 | 1/1966 | United Kingdom | 604/292 |
| 2100581 | 1/1983 | United Kingdom . | |

OTHER PUBLICATIONS

European Search Report of May 29, 1985 in European Patent Application 84,115,656.9 (5 pages).

*Primary Examiner*—Harvey C. Hornsby
*Assistant Examiner*—Joseph S. Machuga
*Attorney, Agent, or Firm*—Thomas J. Mielke

[57] ABSTRACT

The invention relates to a garment shaped to fit bodily extremities, such as the hand, that has a sleeve extending up the extremity. The sleeve is provided with an integral sealing device to close the open end of the sleeve and form a container after being turned inside-out during removal. The garment is removed from the extremity and simultaneously turned inside-out, after which it is sealed with the sealing device. The invention may be adapted for use on either the hands or the feet. In one form the invention is in the shape of a glove, having a widened sleeve, extending at least part way up the arm. The outer portion of one side of the sleeve is provided with an adhesive band such that when the glove is removed, the adhesive band is on the inner portion and may be sealed to the opposite side of the sleeve to form a bag container for disposal.

5 Claims, 6 Drawing Sheets

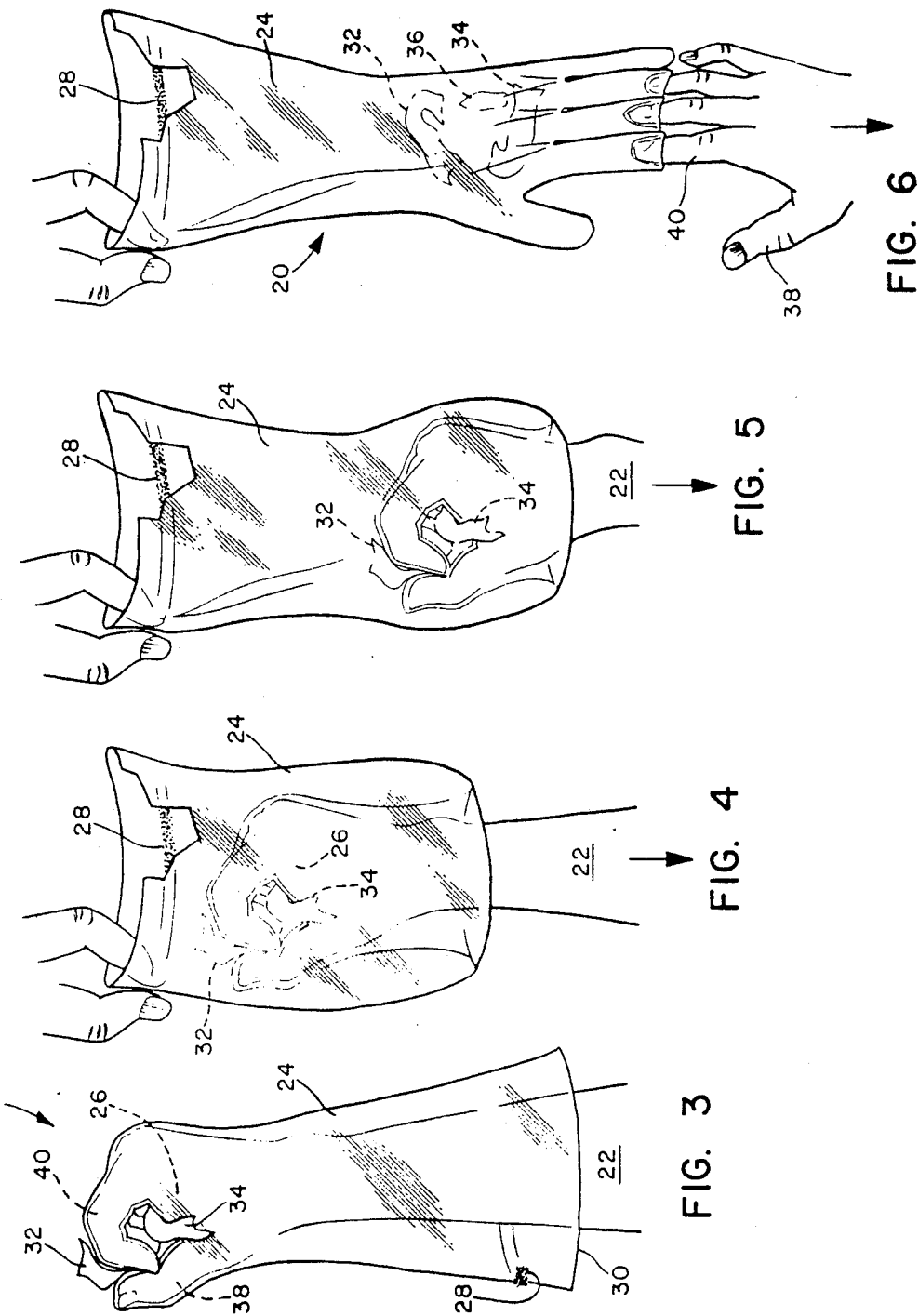

GARMENT DEVICE FOR HANDLING AND STORING NOXIUOS MATERIALS

TECHNICAL FIELD

The present invention relates to a garment-like device that may be worn to allow manipulation of soiled or hazardous material and then when properly removed, becomes a device for storage of the soiled material. In a particular embodiment it comprises a glove garment that may be turned inside-out when removed and has a fastening device attached thereto for sealing of the open end of the inverted glove after removal.

BACKGROUND ART

In the field of health care and handling of hazardous materials it is has been known to utilize disposable flexible gloves that may be worn during the handling of the soiled or hazardous material, removed and then safely disposed of after the task is finished. The disposal of these articles may require special containers in order to prevent fumes from being released after disposal. In the nursing home and home care of incontinent patients there is a continuing problem with odor. Of particular concern is the odor of the wiping rags and cleaning materials used to clean patients during changing of incontinent garment.

It has been proposed in U.S. Pat. No. 4,132,442 to Larsson that the picking up and removing of noxious items may be accomplished by use of a container device fitted onto a plastic bag. It is further proposed that the bag-like sleeve may be folded over the container element attached to the bag in order to form a waste container. A somewhat similar device is proposed in U.S. Pat. No. 3,850,467 to Johnson in which a scoop is attached to the bag whereas in the Larsson patent a combination container and scoop is fastened to the bag. Such devices as in Larsson and Johnson are difficult to manipulate to perform tasks and only suitable for handling large objects. The devices are also expensive to manufacture.

There remains a need for a garment that is suitable for handling of noxious material and which may be disposed of without creating odor problems. Further there is a need for a simple way to dispose of materials that are used in wiping up or other the handling of the noxious material. Further, there is a need for a device that is easily manipulated when serving its protective function but also provides sealed storage of noxious matter when removed.

DISCLOSURE OF THE INVENTION

An object of this invention to provide a protective covering for exposure to noxious materials.

An additional object of this invention to provide convenient storage of materials soiled in changing of incontinent garments.

An object of this invention is to provide a low-cost device for both noxious material storage and protection during manipulation of noxious material.

These and other objects of the invention are generally accomplished by providing a garment-shaped container to fit bodily, extremities, such as the hand, and having an extended sleeve portion extending up the extremity. The sleeve portion is provided with a sealing device to close the open end of the sleeve after the garment is removed from the extremity and by grasping at the edges and simultaneously turned inside-out as it is removed. After removal it is sealed with the sealing device forming a container. The container of the invention may be adapted for use of either the hands or the feet.

In a preferred form the invention container device is in the shape of a glove, having a sleeve, integrally connected with the hand covering and extending part way up the arm. The outer portion of one side of the sleeve, near the glove opening is provided with an adhesive band such that when the glove is removed and turned inside-out, the adhesive band is on the inner portion and may be sealed to the opposite side of the sleeve to form a bag for disposal. The glove is sufficiently large that it may be removed and turned inside-out while holding several soiled rags or wipes in the hand such as would result from the changing of the incontinent care garment of an adult patient. The glove therefore acts as its own container for the soiled rags and material on the glove itself.

BRIEF DESCRIPTION OF THE DRAWINGS

FIG. 3 if a view of a device of the invention worn on a hand and holding wiping cloths.

FIG. 4 is a view of the hand of FIG. 3 with the device of the invention partly removed.

FIG. 5 is a view of the FIG. 3 device of the invention that has been removed from the arm but remains on the hand of the wearer.

FIG. 6 is a view of the FIG. 3 garment of the invention except for the ends of the fingers and containing the wiping cloths.

MODES FOR CARRYING OUT THE INVENTION

The invention has numerous advantages over prior practices, particularly those in the nursing home and home care of incontinent patients. In care of such patients odor is a particular problem, and the provision for a device that simultaneously provides protection from the hands being in repeated contact with excrement and provides a substantially odor-proof method of disposal of rags used in cleaning up incontinent problems is a significant advance over prior methods. Such prior methods require special waste receptacles that have not been completely effective. The disposal garment of the invention further is particularly suitable for the home market where special disposal means are not available and the people caring for incontinent patients may be even less likely to desire contact with excrement and do not have special disposal means available. The device further is expected to find use in the medical field for examination of patients and in the veterinary field for both examination of animals and when the veterinarian is required to walk through barns and temporary foot protection is desirable. These and other advantages of the invention will become apparent from the detailed description as given below.

Figure 1:
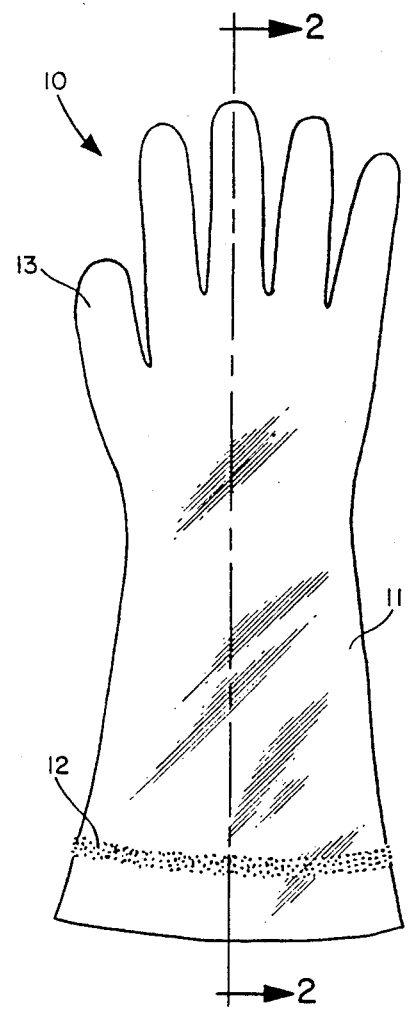
FIG. 1 is a view of the glove in accordance with the invention.
Figure 2:
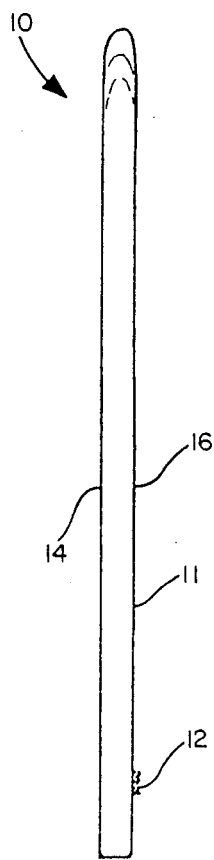
FIG. 2 is a cross-section along line 2—2 of FIG. 1 of a glove of the invention.

As illustrated in FIG. 1, a glove of the invention generally indicated as 10 is composed of a flexible material. The flexible glove material may be formed from films such as polypropylene or polyethylene films or sheets. The glove 10 has four fingers and a thumb 13 to allow easy manipulation of objects held by the hand within the glove. The glove further has a band of adhesive 12 that is located on the exterior of the sleeve portion 11 of the glove when it is worn. The view in FIG. 2 on cross section line 2—2 of FIG. 1 illustrates the thin sheets of polymer 14 and 16 forming the palm and backside respectively of the glove 10.

These gloves may be formed by placing two sheets of polyolefin polymer film together and then simultaneously cutting out the two sheets into the glove shape while fusing the edges together by heat. This is a low-cost very highly-automated method of formation of such gloves. This method of forming articles from fusable films is well known and is believed to now be used in formation of gloves.

FIG. 3 through FIG. 8 illustrate the use of the garment device in accordance with the invention. As illustrated, a glove generally indicated as 20 is shown in FIG. 3 in a soiled condition holding soiled rags. The glove has a sleeve portion 24 in which the arm 22 and hand 26 are placed. The glove further has an adhesive layer 28 on the sleeve portion at a location near the opened end 30. The soiled rags 32 and 34 are held awaiting disposal. As indicated in FIGS. 4 and 5, the sleeve of the glove is removed from the arm and simultaneously turned inside out. In FIG. 6 the glove is shown having been removed from the thumb 38. The glove remains on the fingers 40. In FIG. 6 the rags 32 and 34 as well as fecal matter 36 are contained by the bag-like inside-out garment 20.

Figures 7, 8:
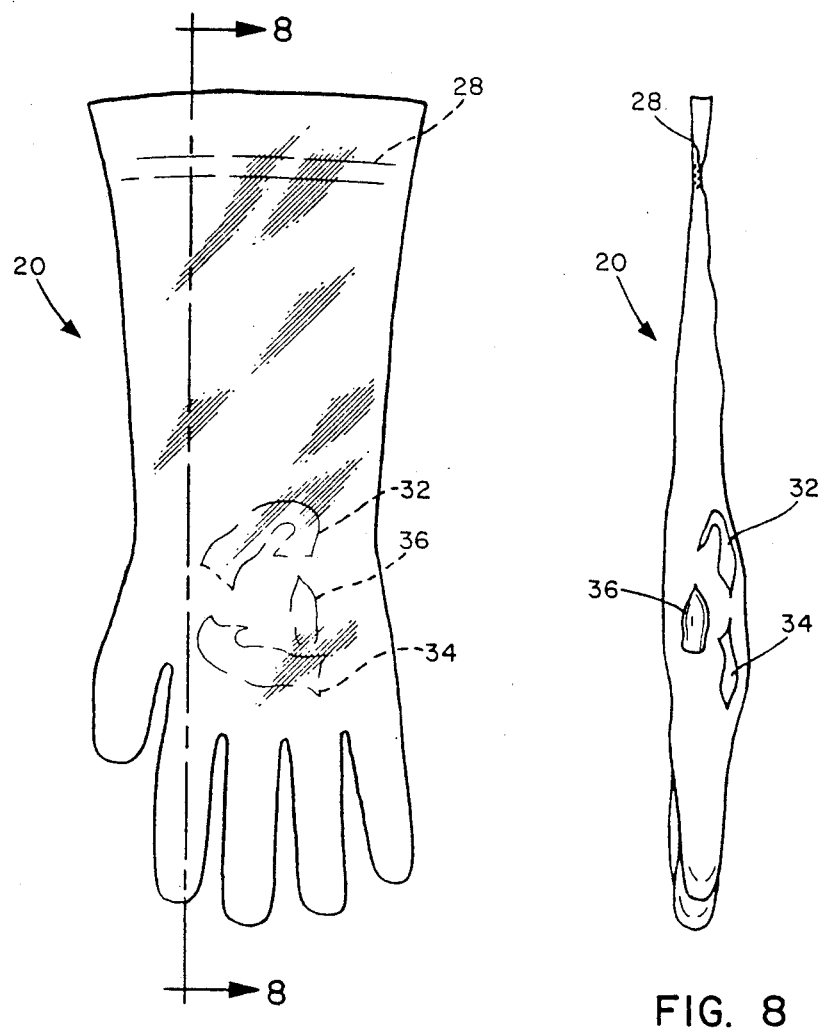
FIG. 7 is a view of the FIG. 3 device of the invention with the wiping rags encased in the device.
FIG. 8 is a cross-sectional view of FIG. 8 along line 8—8 of FIG. 7.

In FIGS. 7 and 8 the glove 20 is illustrated with the top sealed on adhesive line 28 and with the rags 32 and 34 and the feces 36 contained in the sealed bag which will prevent odor and noxious materials from being released. The material is sealed by pressing along the line of pressure-sensitive adhesive 28 to secure adherence of the adhesive-lined portion 28 to the sleeve portion not containing the adhesive.

Figure 11:
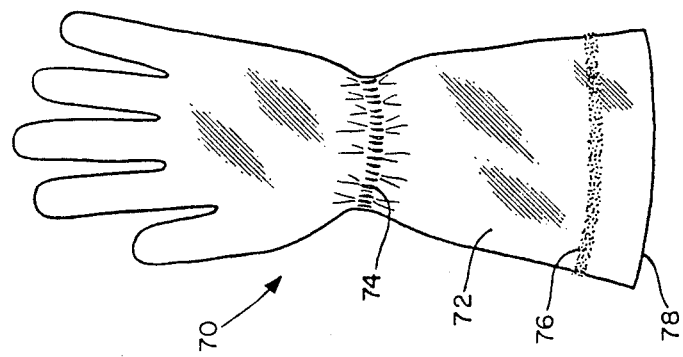
FIG. 11 is a view of an alternative form of the garment of the invention with an elasticized wrist portion.
Figure 10:
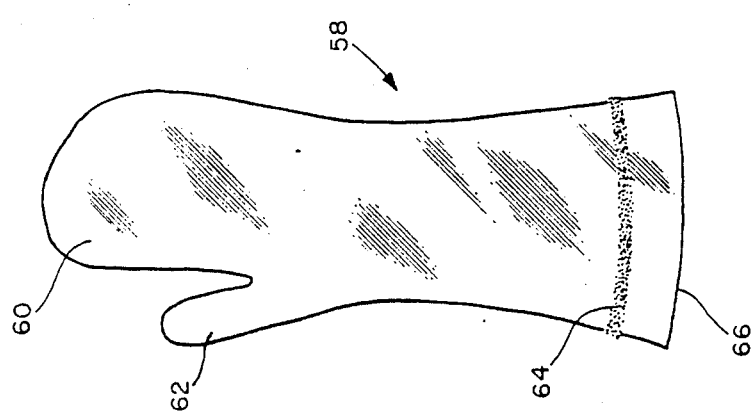
FIG. 10 is a view of an alternative embodiment of the invention device of the invention in the form of a mitten.
Figure 9:
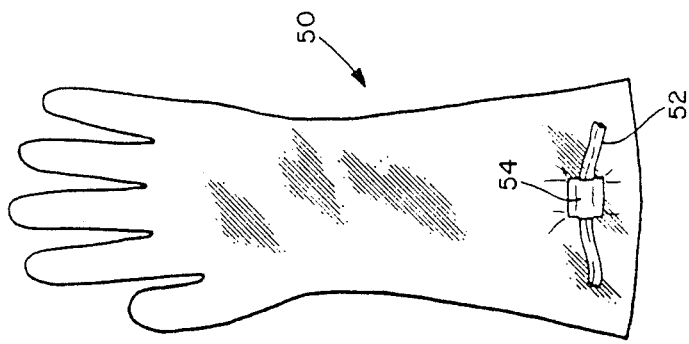
FIG. 9 is a view of an alternative embodiment of the form of a glove.

FIGS. 9 through 13 illustrate various alternative embodiments of garment disposal devices in accordance with the invention. In FIG. 9 is illustrated a glove 50 that has a twist tie 52 adhered thereto by adhesive area 54. FIG. 10 illustrates in alternative embodiment in the form of a mitten 58 for uses where the manipulation of fingers is not required. In this embodiment all fingers are placed in portion 60 with the thumb in portion 62, and a sealing adhesive 64 near the cuff portion 66. In FIG. 11 is illustrated a glove 70 with a long-arm portion 72. The glove of FIG. 11 further has an elasticized wrist 74 and the adhesive band 76. A long-armed glove may be particularly suitable for tasks such as those done by veterinarians. The long-sleeved glove of proper material also could be used when working near open vats of caustic material. The wrist band 74 would aid in holding on the long-sleeved glove. While shown with only one elastic wrist band 74, it would also be possible to put elastic bands on the cuff portion 78 or in the mid portion of the sleeve 72.

Figure 12:
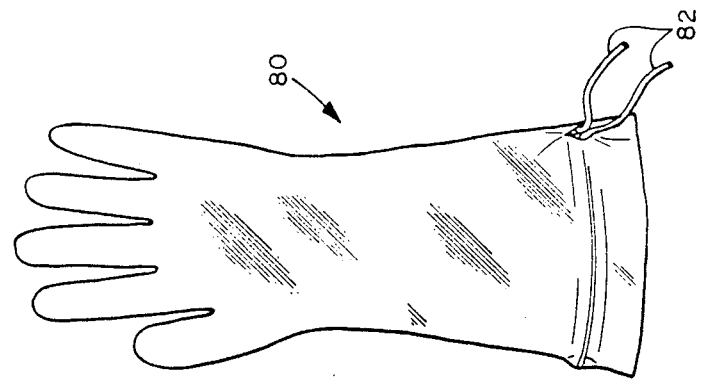
FIG. 12 is a view of a garment in accordance with the invention in which the fastening device is comprised of ties.

In FIG. 12 is illustrated a glove 80 in which the fastening means at the wrist are pull strings 82 that may be tightened after the glove is reversed as it is removed.

Figure 13:
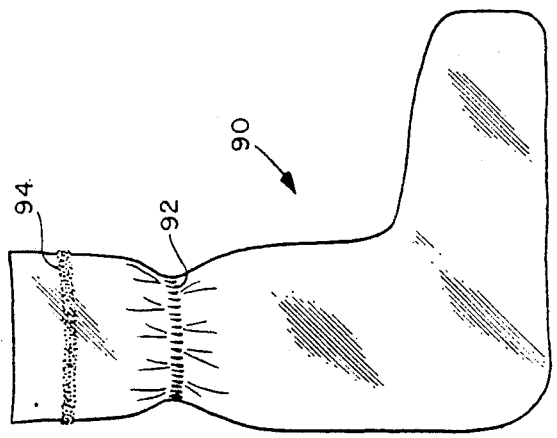
FIG. 13 is a view of a device of the invention adapted for use on the foot and leg.

In FIG. 13 is illustrated a device for protection of the foot and disposal of any noxious materials which may cling to the foot. The device 90 is shaped like a boot and has an elastic band 92 at the ankle portion to aid in keeping it on the foot. There is further an elastic sealing means 94 to seal the boot after it is removed.

Figure 14:
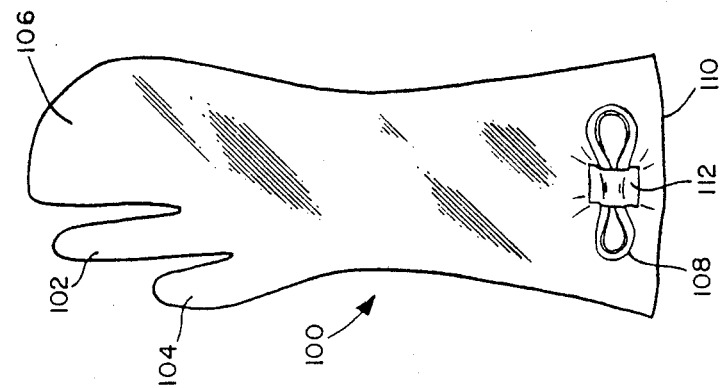
FIG. 14 is a view cf an alternative device of the invention with a one-fingered glove and rubber-band tie.

FIG. 14 illustrates further embodiments in a one-fingered glove over 100 that has the index finger 102 and thumb 104 brought in mitten-like portion 106 for the remaining three fingers. This one-fingered glove is illustrated with a rubber band 108 adhered to the upper cuff portion of the mitten 110 by an adhesive 112.

There have been several means of providing a closing device for the garment, disposal container of the invention illustrated in the drawings. The means is integral with the container and therefore available for sealing immediately after garment is removed. The preferred means is considered to be a band of pressure-sensitive adhesive placed near the cuff on one side of the sleeve portion of the garment as this adhesive is effective and low in cost. This elastic band such as illustrated in FIGS. 1, 10, 11 and 13 would be permanently adhesive and could be pressed against the opposite side of the sleeve after the garment is reversed for sealing. Also it is within the invention to utilize other sealing devices which may be fastened to the reversed exterior of the cuff or sleeve portion of the disposal garment such as twist ties, strings, tape, rubber bands or the tongue-and-groove sealing devices such as used in the bags sold under the trade name ZIPLOC by Dow. It further would be possible to utilize a pressure-sensitive adhesive, such as those used for feminine pads, that is covered prior to reversal by a piece of paper which would be removed to expose the adhesive. The paper after removal could be inserted into the glove for disposal with any other debris. The composition of pressure-sensitive adhesives is known. Typical of such adhesive are the so-called cohesive adhesives formed of natural rubber latex tackified with resin esters. Pressure-sensitive adhesives such as those of U.S. Pat. No. 4,234,662 based on acrylate ester homo- and copolymers are also suitable. that melt adhesives such as those disclosed in U.S. Pat. Nos. 3,932,328 and 4,028,292 also would be suitable. The pressure-sensitive adhesives are generally formed of block copolymers, such as those of styrene and an elastomeric component, combined with a tackifier such as a liquid hydrocarbon resin. A tape closure means similar to those utilized in a diaper, in which a covering is placed over the tape's adhesive and removed by the mother prior to fastening the diaper also would be suitable.

The disposal garments of the invention may be formed of any generally impervious material. The material must be flexible. Typical of such materials are: polymer sheet materials such as polyvinyl chloride, polyethylene terephthalate, other polyesters or acrylic sheet materials. The preferred materials are films of polyethylene or polypropylene, as these materials are very low in cost and may be easily formed with heat sealing of the edges of the two sheets when they are cut to shape; heavier duty materials also could be utilized with rubber gloves or rubber- or metal-coated cloth-reinforced rubber gloves for special purposes where cost is not as great a consideration such as in disposal of hazardous chemicals or radioactive material.

The shape of garment may be any desired shape which is comfortable for the wearer and allows the wearer to perform the task required. A preferred shape is illustrated as the shape of a glove, mitten, or one-fingered glove. The sleeve portion may be any desired length, and in special uses could extent up to the shoulder for the device worn on the arm, and to the crotch for shoe covers or boots.

It is further desirable in some instances that the garments could have one or several strips of elastic to tighten the sleeve portion and make it more convenient, and better able to stay on the arm or leg during use.

Figure 15:
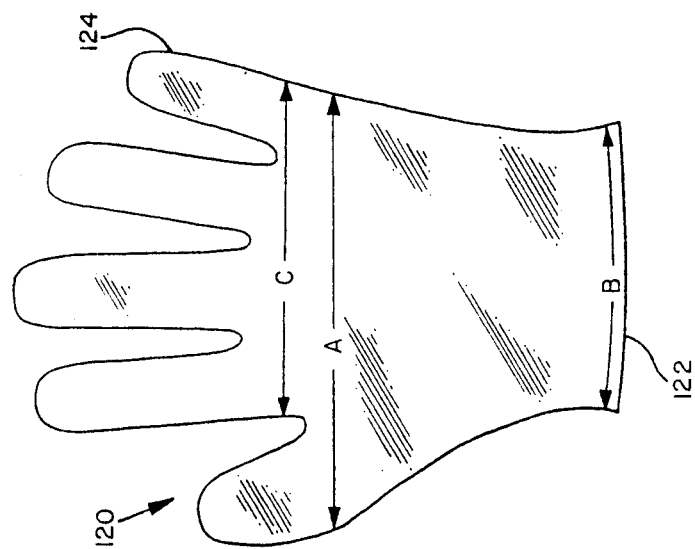
FIG. 15 is a view of a container of the invention in the form of a glove with a sleeve portion adapted to cover the wrist.

In formation of the garment of the invention, the sleeve portion generally is wider than that ordinarily utilized in formation of plastic protective gloves or boots. The device must be large enough in the sleeve portion to allow the easy reversal and withdrawal over the hand or foot portion without close contact. The sleeve should be able to easily pass over, with minimum contact, a hand-held in a loose fist. In a medium adult glove that extends about 2-about 4 inches above the hand, the upper portion would be about 6 or about 7 inches across the top when laid flat to allow sufficient room for hand withdrawal and reversal of the glove. The hand should be able to be withdrawn when at least slightly clutched into a fist. Generally, the glove or mitten when laid flat would be between about 5.5 and about 7 inches across in the area of four finger knuckles of the hand, and would be between about 5 and about 7 inches across the top or open end at the cuff portion when laid flat. FIG. 15 illustrates a glove of the invention 120 that has the cuff 122 extending about 2 to about 4 inches up the wrist. The A line represents the measurement across the area of the five knuckles of the hand including thumb 124. The B measurement is across the open cuff 122. The C measurement is across the area of the four finger knuckles. The Table 1 below sets forth preferred measurements for three typical sized gloves of the invention. The glove is laid flat when measured. The ratio of wrist width to the four knuckle width is about 1 to 1.

TABLE 1

GLOVE MEASUREMENT - GLOVE LAID FLAT

| Size | (A) Across 5 Knuckles | (B) Across Cuff | (C) Across 4 Knuckles |
|---|---|---|---|
| Small | 6¾" | 5¼" | 5¾" |
| Medium | 7¾" | 6⅛" | 6¼" |
| Large | 9¼" | 6¾" | 7" |

Figure 16:
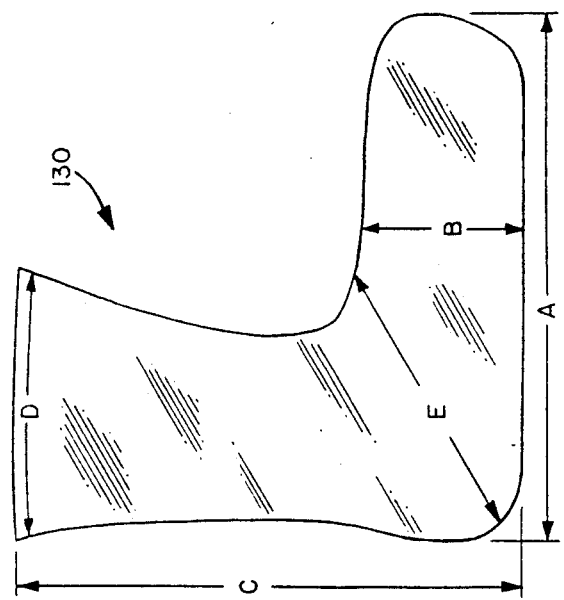
FIG. 16 is a view of a container of the invention for foot protection.

A boot-like garment to form a container for noxious materials on the foot should be wide enough at the open cuff portion that it may be withdrawn over the foot without dislodging material clinging to the boot. FIG. 16 illustrates a foot covering container 130 with measurement lines A, B, C, D and E indicating areas to be considered in formation of a foot covering container. The measurements are for the container laid flat and generally are one-half the circumference in the area measured. Table 2 below sets forth preferred sizes for the foot covering and waste container of the invention.

TABLE 2

BOOT LAID FLAT

| Size | A Foot Length | B Foot Height (½ ft. circumference) | C Heel to Cuff | D Cuff Width | E Heel Over Instep (½ circumference) |
|---|---|---|---|---|---|
| Small | 8.5-12.5 | 5-6 | 6½-10 | 8-9 | 8-8½ |
| Med. | 9.5-14.5 | 6-7½ | 10-13½ | 9-9½ | 8½-8¾ |
| Large | 11½-18 | 7½-8½ | 13½-17 | 9½-12 | 8¾-9½ |

The device of the invention may find utility in a variety of industries and may be used for a variety of purposes in the home. It will find utility in food preparation where odor prevention and sanitary needs demand a disposal container which is sealable. Further, there is need for the garment disposal device in chemical handling and in handling of radioactive material. The device could also be utilized in personal hygiene or for general house and garden work. Another use would be in the vocation of hair coloring which has a large amount of odor and further colors anything it comes in contact with during the disposal process. This advantage would apply to any use in the field requiring dyes, their disposal, and crossing of colors. The disposal garment of the invention also would be desired in the pharmaceutical trade and other industries where clean rooms are utilized.

While the invention has been illustrated with specific embodiments, it is contemplated that those of skill in the pertinent fields will recognize modifications and alterations within the invention are possible. For instance, other fastening devices could be utilized to fasten the sleeve portion after removal. Further there could be devices to tighten the large upper wrist portion during use. Further, various combinations of fastening devices, elastic wrist portions and number of fingers are possible. Also, handling of differing hazardous materials may require special glove materials. The scope of the invention is only intended to be limited by the attached claims.

I claim:

1. A method of disposal comprising placing onto an arm a container comprising a hand and arm conforming glove of flexible polymer sheet covering adapted to fit the hand and having an extended sleeve portion extending along the arm at least partially to the body and a fastening means integrally formed with said covering adapted to close the open end of said container when it is removed from the bodily extremity, performing a task in which the exterior of said covering becomes soiled, removing said container from the extremity while inverting said container so that the exterior of said container becomes the interior and closing the open end of the inverted device with said fastening means, wherein said fastening means provides an odorproof seal, said covering is about 5.5 to about 7 inches across in the area of the four knuckles and about 5 to about 7 inches across the cuff portion when laid flat and wherein the ratio of knuckle width to cuff width is about 1 to 1.

2. The method of claim 1 further comprising an elasticized portion of said glove adapted to hold said sleeve around the arm.

3. The method of claim 1 wherein said task is changing an incontinent garment.

4. The method of claim 1 wherein said closing of the open end of said container is accomplished by an adhesive strip on one interior side of the inverted device being pressed against the opposite interior side of the device.

5. The method of claim 4 wherein said adhesive strip is covered by a removable paper covering.

* * * * *